United States Patent [19]

Müller et al.

[11] Patent Number: 5,128,094
[45] Date of Patent: Jul. 7, 1992

[54] TEST INSTRUMENT MANIPULATION FOR NUCLEAR REACTOR PRESSURE VESSEL

[75] Inventors: Günter Müller, Nürnberg; Heinz-Josef Otte, Wendelstein; Werner Roth, Neuendettelsau, all of Fed. Rep. of Germany

[73] Assignee: MAN Energie GmbH, Nürnberg, Fed. Rep. of Germany

[21] Appl. No.: 638,830

[22] Filed: Jan. 8, 1991

[30] Foreign Application Priority Data

May 5, 1990 [DE] Fed. Rep. of Germany ....... 4014161

[51] Int. Cl.⁵ .......................................... G21C 17/013
[52] U.S. Cl. .................................... 376/249; 376/245
[58] Field of Search ................ 376/245, 249, 260, 271

[56] References Cited

U.S. PATENT DOCUMENTS

| 4,081,325 | 3/1978 | Aubert et al. ................ 176/87 |
| 4,169,758 | 10/1979 | Blackstone et al. .............. 176/19 R |
| 4,507,260 | 3/1985 | Fujimoto et al. ................ 376/249 |
| 4,518,560 | 5/1985 | Takaku et al. ................ 376/245 |
| 4,585,610 | 4/1986 | Andersson et al. ............. 376/249 |

FOREIGN PATENT DOCUMENTS

| 3112201 | 10/1982 | European Pat. Off. . |
| 3235297 | 4/1983 | European Pat. Off. . |
| 3524390 | 1/1987 | European Pat. Off. . |
| 0015556 | 1/1985 | Japan ................ 376/249 |
| 2000854 | 1/1987 | Japan ................ 376/249 |
| 0010915 | 3/1990 | Japan ................ 376/245 |
| 2159227A | 11/1985 | United Kingdom . |

OTHER PUBLICATIONS

"Inspection Approach for Future Reactors", *Nuclear Engineering International*, Oct. 1976, pp. 68-71.

*Primary Examiner*—Brooks H. Hunt
*Assistant Examiner*—Chrisman D. Carroll
*Attorney, Agent, or Firm*—Spencer, Frank & Schneider

[57] ABSTRACT

A device for non-destructive testing of an upright cylindrical nuclear reactor pressure vessel in which there is disposed a coaxially arranged likewise cylindrical nuclear fuel container. A first upper annular rail is fastened to an upper edge of the pressure vessel. A second lower annular rail is fastened to an upper edge of the nuclear fuel container. A bridge element is displaceably mounted on the first annular rail. A vertical, hollow mast projects into the pressure vessel and has an upper end mounted at the bridge and a lower end movably mounted to said second annular rail so that the mast is movable in a circumferential direction of the pressure vessel. A deflectable belt is disposed for longitudinal displacement through the hollow mast. The belt exits the hollow mast at a lower region of the mast and has an end extendable into an annular space between an inner wall surface of the pressure vessel and an outer wall surface of the nuclear fuel container. A test instrument carrier is mounted at the end of the belt.

14 Claims, 11 Drawing Sheets

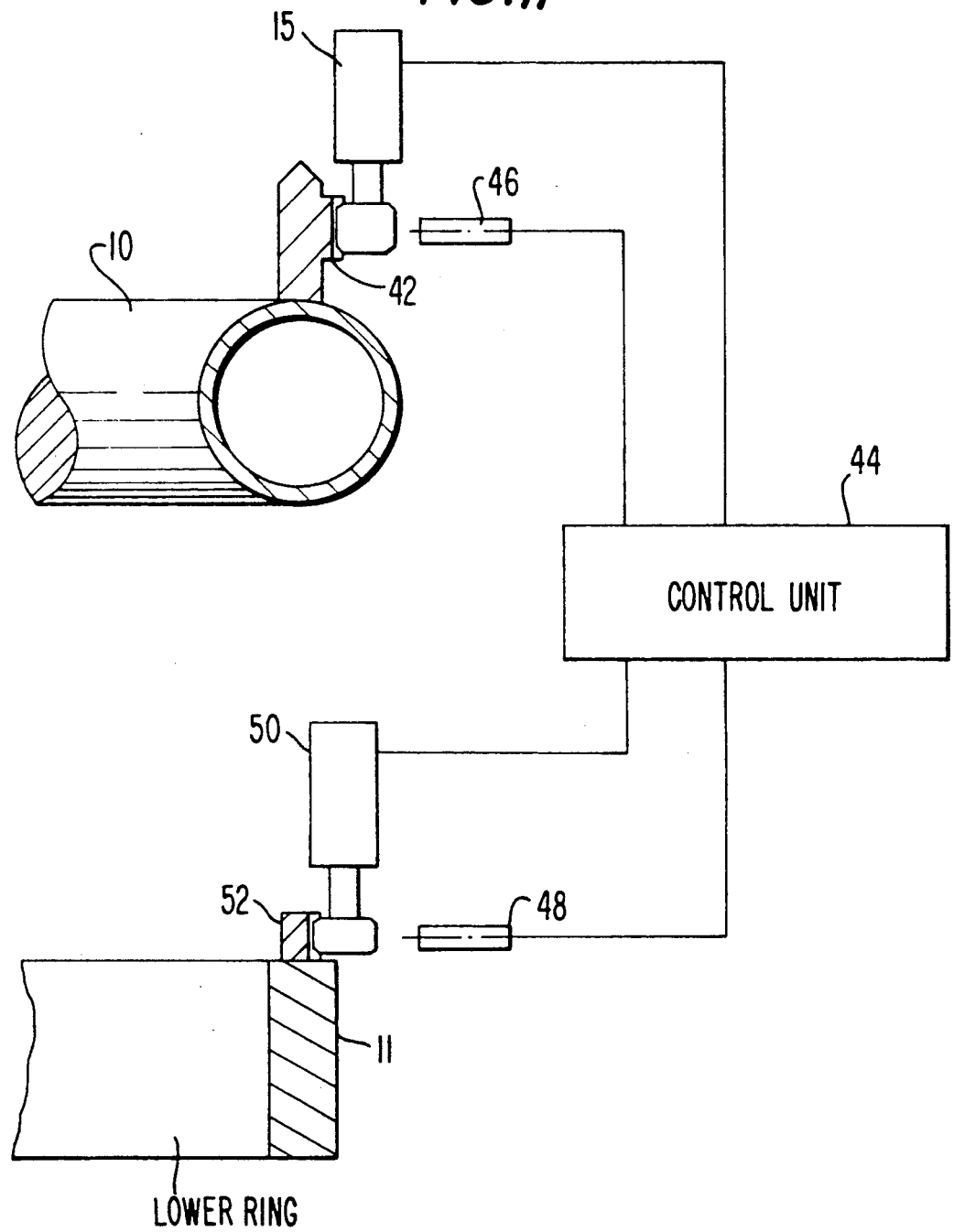

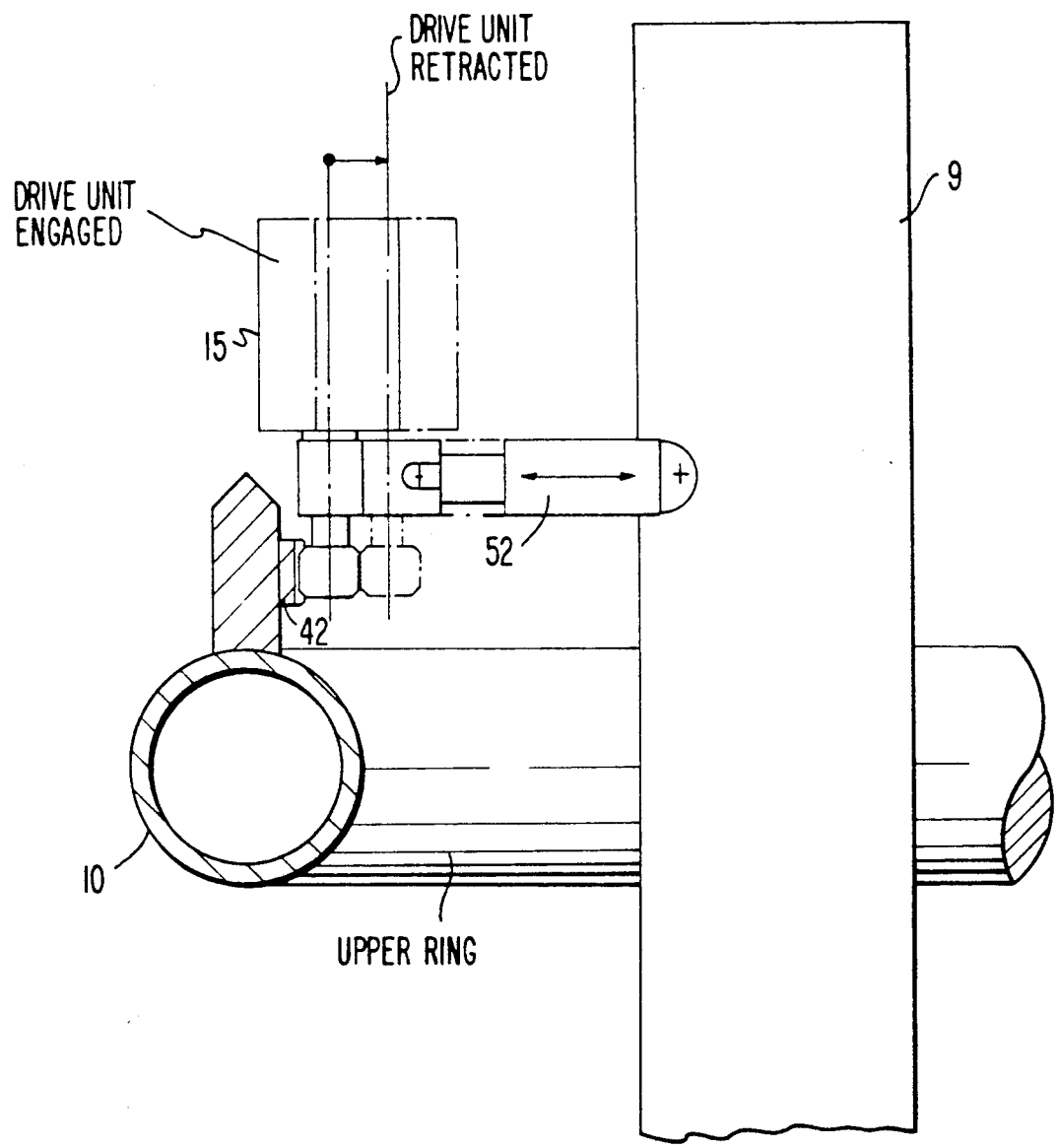

TEST INSTRUMENT MANIPULATION FOR NUCLEAR REACTOR PRESSURE VESSEL

CROSS REFERENCE TO RELATED APPLICATION

The present application claims the right of priority with respect to application Ser. No. P 40 14 161.6, filed May 3rd, 1990, in the Federal Republic of Germany, the disclosure of which is incorporated herein by reference.

BACKGROUND OF THE INVENTION

The present invention relates to a device for the non-destructive testing of an upright cylindrical nuclear reactor pressure vessel in which a likewise cylindrical coaxial nuclear fuel container is disposed. The device includes a vertical mast projecting into the pressure vessel and mounted so as to be displaceable at its upper and lower ends in the circumferential direction of the pressure vessel. The mast is equipped with a carrier for test instruments which can be displaced along the mast. Devices of this type are disclosed, for example, in German Offenlegungsschrift [laid open patent application] No. 2,644,261 and corresponding U.S. Pat. No. 4,081,325.

The pressure vessels of nuclear reactors are known to be composed of several bent, plate-shaped or preferably annular components, with the components being interconnected by weld seams. The weld seams and the parts of the plates immediately adjacent the seams constitute critical regions in the pressure vessel since, due to inclusions, blowholes or bubbles, brittlenesses and other faults, they may include zones of lower strength. For this reason it is absolutely necessary to test the entire pressure vessel, and particularly the above-mentioned zones, for freedom from faults before it is put into operation for the first time and also during its operation. This is generally done with the aid of ultrasonic devices which detect and localize inclusions and blowholes due to their echo behavior which differs from the remainder of the material. To perform such tests, it is necessary to guide the test instrument with great accuracy along the interior or exterior wall of the pressure vessel and to provide means which continuously, and with great precision, record the position of the test instrument. The technical difficulties arising in this connection become evident if one realizes that the height of such a pressure vessel may be 10 meters and more. The manipulator which guides the testing devices and brings them to their locations of use, must be able to indicate the respective position of the test instrument with an accuracy of ±3 mm.

The aforementioned mentioned German Offenlegungsschrift No. 2,644,261 and corresponding U.S. Pat. No. 4,081,325 disclose a test manipulator which is essentially composed of a vertically arranged mast that is mounted so as to be movable on running rails disposed at its upper and lower end. The running rails are angularly arranged around the cylindrical nuclear fuel container so that the mast can be displaced circumferentially with good guidance from the top and bottom. A vertically displaceable carrier for the test instruments is mounted at the mast. The entire device is disposed in the gap between the nuclear fuel container and the inner wall of the pressure vessel and is of relatively simple construction.

Test manipulators of this type can be used only if reactor constructions are involved in which the annular space between the nuclear fuel container and the inner wall of the pressure vessel does not include any interfering, built-in structures, such as conduits or other fittings. This is frequently the case in more modern reactor designs. However, numerous older designs exist which do not meet this requirement so that manipulators of this type cannot be used in such cases.

SUMMARY OF THE INVENTION

It is an object of the present invention to modify the prior art test manipulators for pressure operated nuclear reactors so that they can also be used in reactors in which the test instrument must be guided into relatively narrow gaps, with it being possible to navigate around obstacles formed by built-in structures and other constrictions in the pressure vessel.

The above and other objects are accomplished according to the invention by the provision of a manipulator device for use in non-destructive testing of an upright cylindrical nuclear reactor pressure vessel in which there is disposed a coaxially arranged likewise cylindrical nuclear fuel container, including: a first upper annular rail fastened to an upper edge of the pressure vessel; a second lower annular rail fastened to an upper edge of the nuclear fuel container; a bridge element displaceably mounted on the first annular rail; a vertical, hollow mast projecting into the pressure vessel and having an upper end mounted at the bridge and a lower end movably mounted to the second annular rail so the mast is movable in a circumferential direction of the pressure vessel; a deflectable belt disposed for longitudinal displacement through the hollow mast, the belt exiting the hollow mast at a lower region of the mast and having an end extendable into an annular space between an inner wall surface of the pressure vessel and an outer wall surface of the nuclear fuel container; and a first test instrument carrier mounted at the end of the belt.

Thus, in accordance with the invention, the vertical mast does not extend into the narrow annular gap between the nuclear fuel container and the inner wall of the pressure vessel; rather it is moved into the space above the nuclear fuel container. Preferably, the upper annular rail is removably disposed at the reactor and is used only if a test is to be made. The deflectable belt is able to reach the narrow annular space in the region between the nuclear fuel container and the inner wall of the pressure vessel, which may possibly be additionally constricted by built-in components, conduits and fittings, and can be moved with sensitivity in the circumferential direction, in the vertical direction and also in the radial direction.

In order to bridge the radial difference existing between the lower annular rail disposed on the nuclear fuel container and the upper annular rail, the upper guidance of the vertical mast moves on a bridge. This bridge is driven by, preferably, a switchable electric drive motor which is in operative connection with a gear on the upper annular rail. In a preferred embodiment, the drive motor or a part connected therewith, is able to act by way of coupling members on a drive mechanism disposed at the lower end of the mast. In this way, it is possible to perform an accurate double control which improves the precision of the guidance for the entire device. In principle, the coupling members may be of the mechanical type; however, at the present state of the art, electronic coupling members are preferred, for example those which scan an incremental scale disposed in the region of the upper annular rail and which transfer the thus obtained digital measurement to a corresponding control device at the lower rail.

The deflectable belt disposed in the interior of the vertical mast and exiting at its bottom is preferably a link chain as known per se, for example from British Patent Application No. 2,159,227. Instead of a link chain, however, other flexible materials can also be employed, for example a correspondingly dimensioned metal belt, for example of stainless steel, or also a fabric or a braided belt. The significant factor is only that the belt must be flexible, that is deflectable, toward the inner wall of the pressure vessel, and that it is not very deformable, that is it is form-stable, in the direction perpendicular thereto.

According to a further aspect of the invention, the first carrier disposed at the end of the deflectable belt is laterally displaceable. This arrangement opens up the possibility that the carrier together with the test instrument disposed thereon can be introduced into gaps which are not accessible to the deflectable belt since built-in components and obstacles are found therebetween. The belt is then dropped next to these built-in components and the carrier at the end of the belt, due to its lateral mobility, can be moved into gaps disposed behind the built-in components. For this purpose, it is of advantage for the first carrier to be connected with the end of the belt way of a two-part telescoping member whose tubes can be driven in a coordinated manner. Such a two-part telescoping member offers the advantage of great stability also in the extended state and makes it possible to connect the carrier and the test instruments disposed thereon with the current source by means of flat cables.

For the performance of ultrasonic tests in the interior of pressure vessels, and also for the performance of other possible tests, for example by means of X-ray devices, it is absolutely necessary that the test heads of the test instruments be brought close to the surface to be tested and are pressed against such surfaces. In order to make this possible without adversely affecting the easy and accurate displaceability of the manipulator, the carrier at disposed, according to yet another aspect of the invention, at the end of the deflectable belt with hydraulic reaction control jets which press it and the test instrument attached to it, against the inner wall of the pressure vessel.

When using the manipulator according to the present invention, it is required that not only the vertical mast be guidable and positionable with the greatest accuracy but also the deflectable belt. Moreover, it is also necessary that this belt be substantially freely manipulatable, with positioning in the circumferential direction being effected by the movable mast. The positioning in the radial direction must be ensured, however, by additional devices. For this purpose, it is another aspect of the invention that, in the lower region on its side facing the inner wall of the pressure vessel, the mast is provided with a guide opening for the belt and in the region between this guide opening and the lower drive mechanism, an adjustable swivel guide is disposed with which the belt can be deflected in the direction of the inner face of the pressure vessel.

In order to make it possible to test regions of the inner wall of the pressure vessel which cannot be reached by the deflectable belt, it is a further aspect of the invention to provide, at least at one narrow side of the mast, at least one second carrier to accommodate test instruments. This carrier is arbitrarily movable in the direction of the longitudinal mast axis, and toward the interior surface of the pressure vessel laterally to the longitudinal center axis of the mast and, rotationally about the operating axis of the test instrument. Thus, this second carrier essentially goes into action whenever it is important to test the region above the nuclear fuel container. In a certain region, the testing regions overlap.

When working with the disclosed manipulator, it may be desirable for the second carrier together with the test instruments disposed thereon to be removed during operation of the manipulator, for example, in order to make changes to the testing system. In this connection, it is another aspect of the invention that the second carrier, including its rotary drive, be removable by means of a lance. The lance may be introduced from the top and pushed into a guide funnel. After introduction, the lance is arrested by means of a quarter or half turn, with the connection of the carrier with the carrier receptacle simultaneously being released. The entire unit may be pulled up by means of the lance and may be removed from the top of the reactor vessel.

BRIEF DESCRIPTION OF THE DRAWINGS

The invention will now be described in greater detail with reference to the accompanying drawing figures.

FIG. 11 shows a block diagram of electronic coupling of drive mechanisms at upper and lower rails.

FIG. 12 is a schematic which shows the drive mechanism on the bridge.

DETAILED DESCRIPTION OF THE PREFERRED EMBODIMENTS

Figure 1:
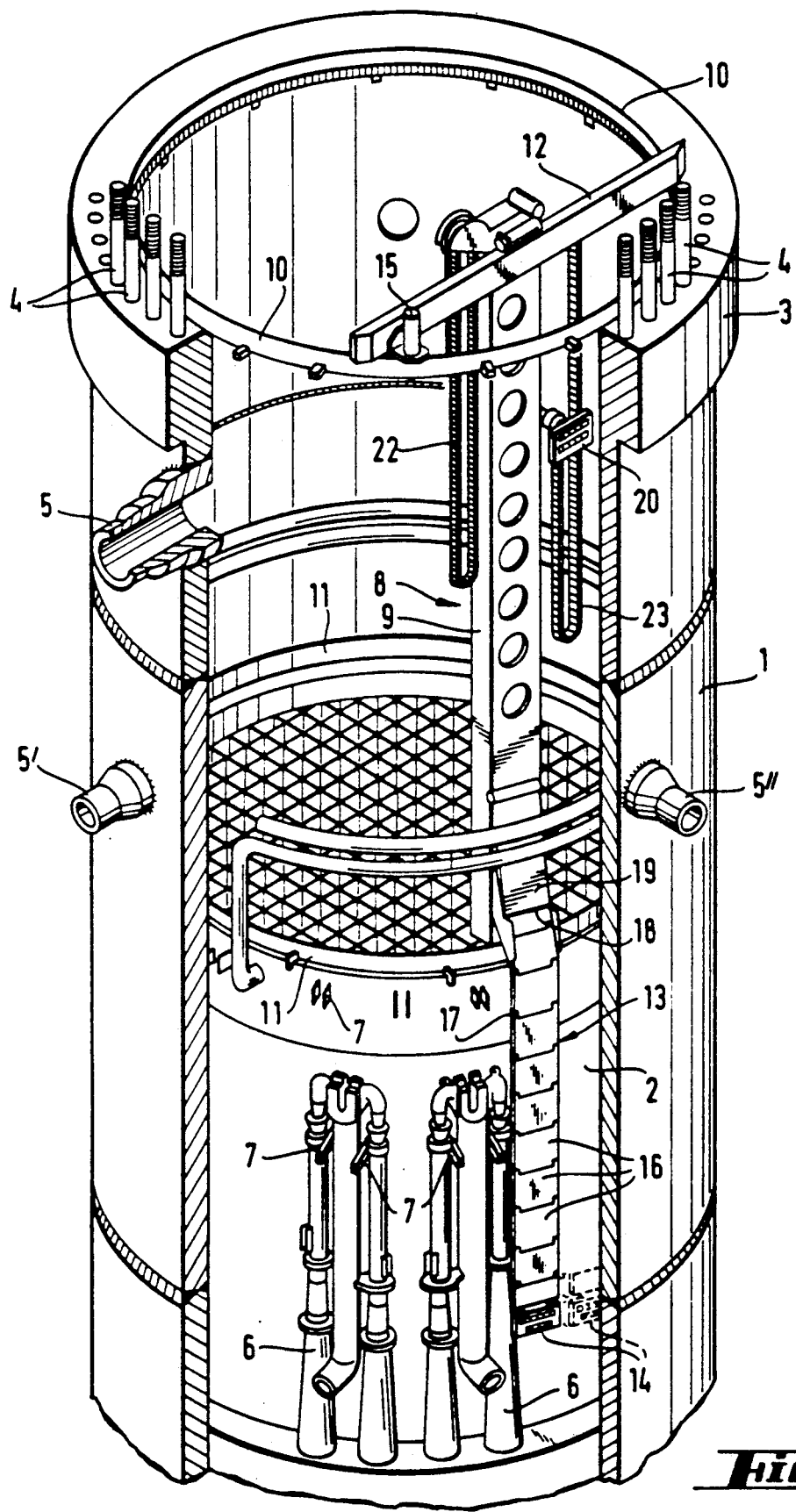
FIG. 1 is a perspective overview of a nuclear reactor pressure vessel, partially cut open, with the manipulator according to the invention inserted.

FIG. 1 shows an upright cylindrical nuclear reactor pressure vessel 1 in which there is disposed a coaxially arranged, likewise cylindrical nuclear fuel container 2. At its upper end, pressure vessel 1 is provided with a flange 3 on which a cover (not shown) is placed during operation. Pressure vessel 1 is provided with several pipe stubs which are indicated exemplarily only at 5, 5' and 5". These pipe stubs and any other desired locations at pressure vessel 1 must be accessible for testing by means of suitable test instruments, usually ultrasonic devices. Particular difficulties are created by built-in components 6 disposed in the narrow annular space between nuclear fuel container 2 and the inner wall of pressure vessel 1. Braces 7 in this region constitute further obstacles for the introduction of the test instruments.

Figure 14A:
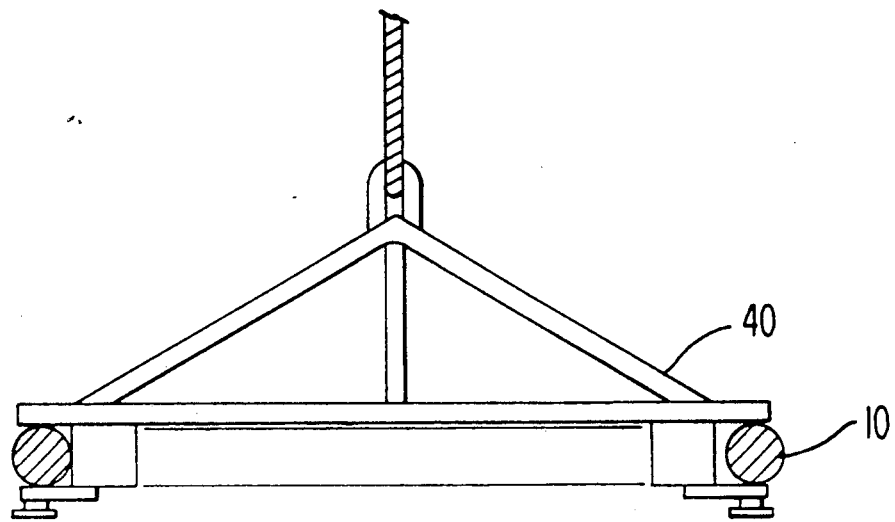
FIGS. 14A and 14B are schematics illustrating the removable upper rail.
Figure 14B:
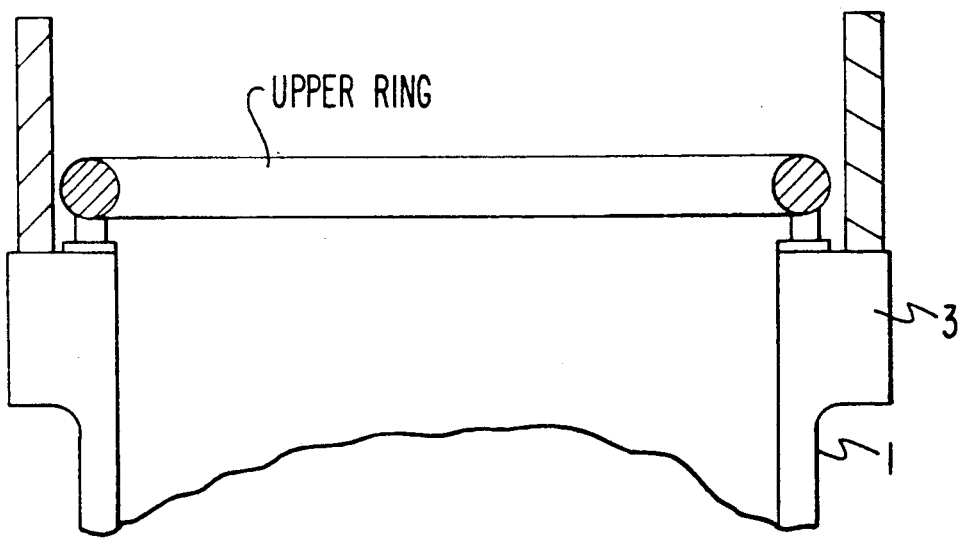

FIG. 1 shows a manipulator 8 which includes a vertical mast 9. At its upper and lower ends, mast 9 is mounted so as to be movable in the circumferential direction of the pressure vessel, namely on a temporarily installed upper annular rail 10 and on a temporarily installed lower annular rail 11. Upper annular rail 10 is provided with a bridge 12 which forms a secant to upper annular rail 10 and is dimensioned so that mast 9, which is movably mounted thereon, is set back in the radial direction until it is possible to circumvent obstacles such as, for example, pipe conduits disposed in the interior of the pressure vessel, with sufficient clearance. Upper annular rail 10 is removably fastened, by suitable means, to the upper surface of flange 3, pressure vessel 1 and is placed there by a lifting beam 40 merely for testing purposes as schematically illustrated in FIGS. 14a and 14b.

At its lower end, mast 9 is displaceably mounted on second (lower) annular rail 11 which, in turn, is removably fastened by suitable means at the upper edge of nuclear fuel container 2. Mast 9 is configured as a hollow rail in whose interior there is disposed a belt 13 which is displaceable in the longitudinal direction and deflectable in the direction toward the inner wall of the pressure vessel. This belt exits from the lower region of mast 9 and extends into the annular space disposed between the inner wall surface of pressure vessel 1 and the outer wall surface of nuclear fuel container 2. At the end of belt 13, there is disposed a first carrier 14 for a test instrument.

Referring additionally to FIG. 11, bridge 12 includes a switchable electric drive motor 15 which is in operative connection with a ring gear 42 (see FIG. 11) attached to upper annular rail 10 and, by way of electronic coupling members including a control unit 44 and sensors 46 and 48, acts on a switchable electronic drive motor 50 at the lower end of mast 9 which similarly engages a ring gear 52 attached to second annular rail 11. FIG. 12 shows an alternative embodiment wherein drive motor 15 is connected to mast 9 by a cylinder 52 for extending and retracting the drive motor for purposes of engagement or disengagement with gear 42.

In a preferred embodiment illustrated in the drawing, belt 13 is a link chain. This chain is composed of individual chain links 16 which are connected with one another by way of joints 17 disposed therebetween. The connection must be precision worked so that the chain can be deflected in the direction toward the inner wall of the pressure vessel but not in a direction perpendicular thereto. The individual chain links generally have a width from 300 to 500 mm and a length of about 600 mm. The first carrier 14 disposed at the lower end of deflectable belt 13 is laterally movable as shown in broken lines in FIG. 1. In its lower region on the side oriented toward the inner wall of the pressure vessel, mast 9 is provided with a guide opening 18 for belt 13, and in the region between this guide opening and lower annular rail 11 with an adjustable swivel guide 19 with which belt 13 can be deflected into the direction of the inner wall surface of pressure vessel 1.

Figure 2:
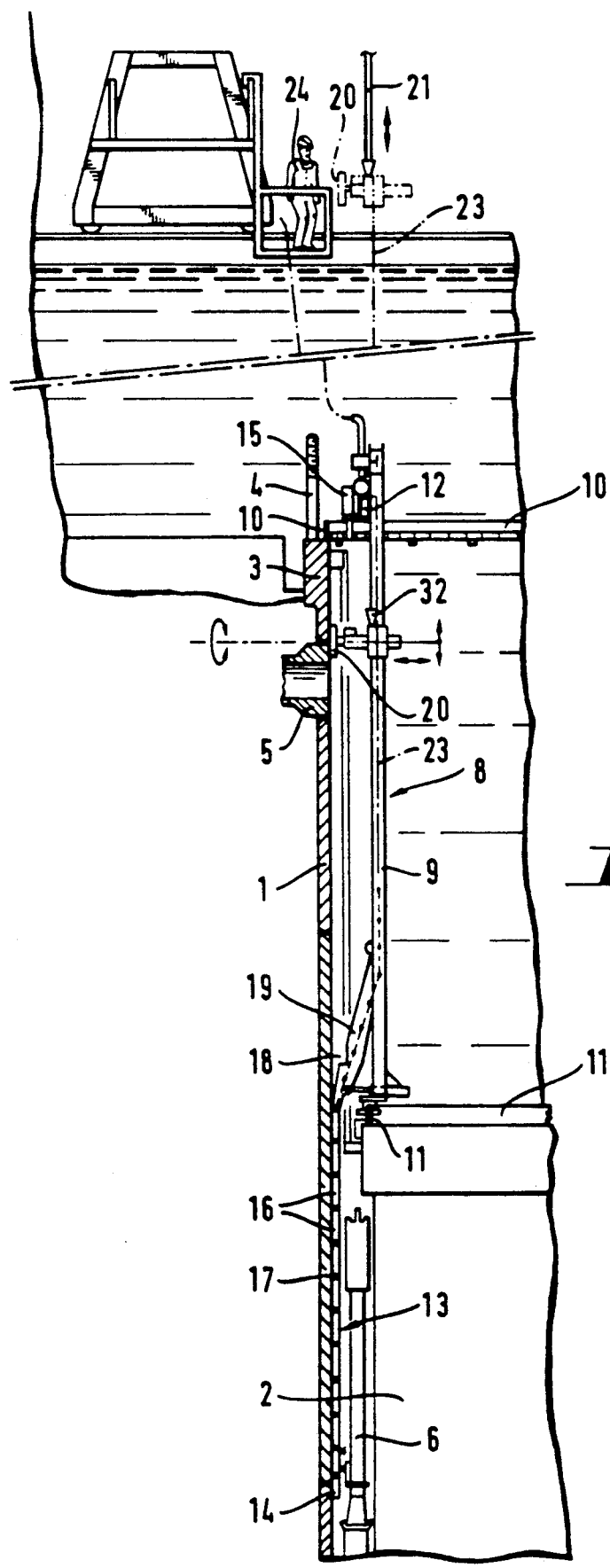
FIG. 2 is a side view of the manipulator shown in FIG. 1.
Figure 3:
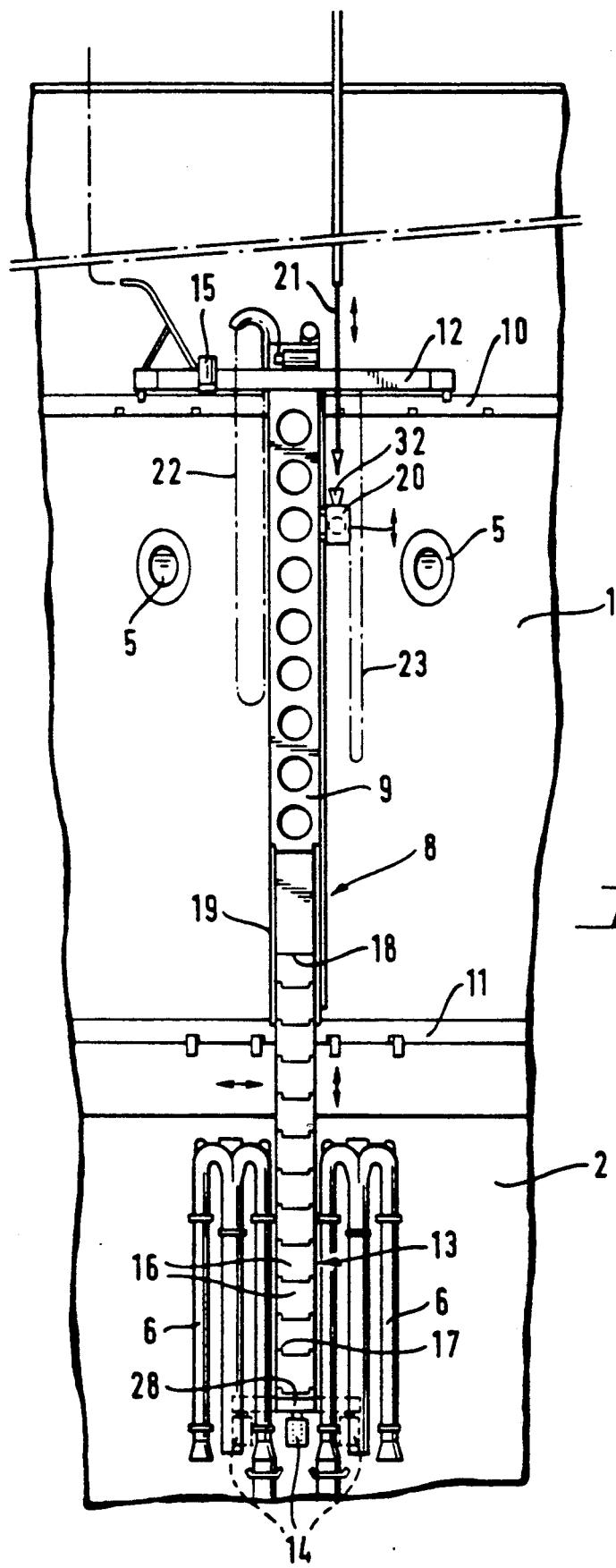
FIG. 3 is a front view of the manipulator shown in FIG. 1.
Figure 13A:
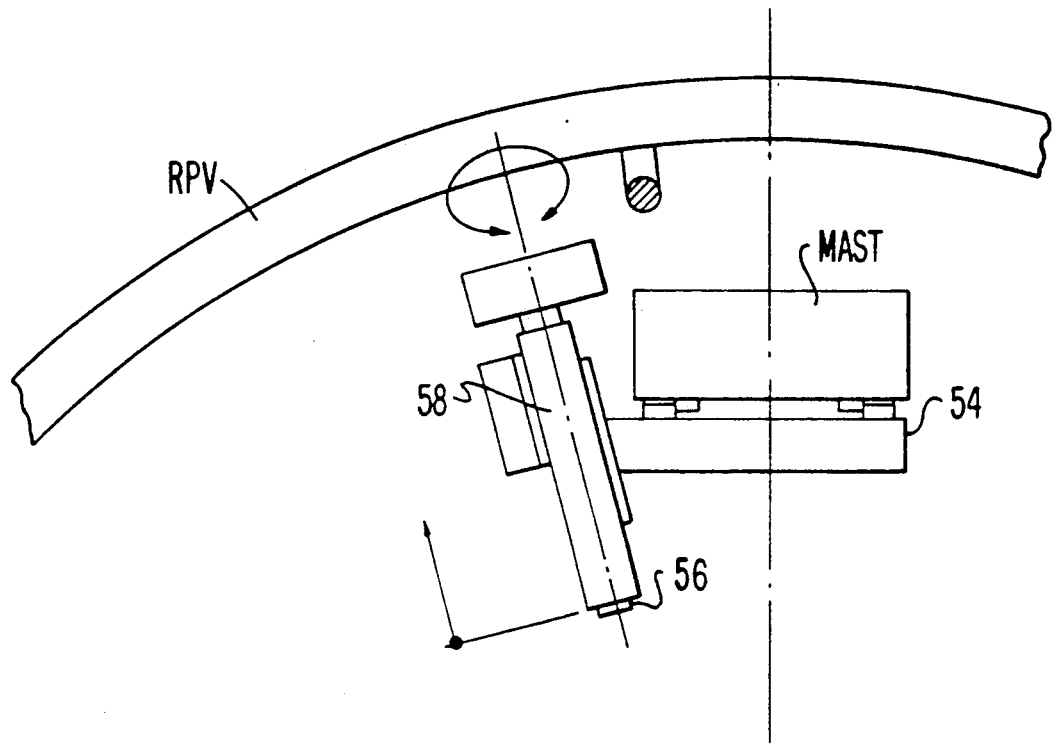
FIGS. 13A and 13B are schematics which show the second carrier.
Figure 13B:
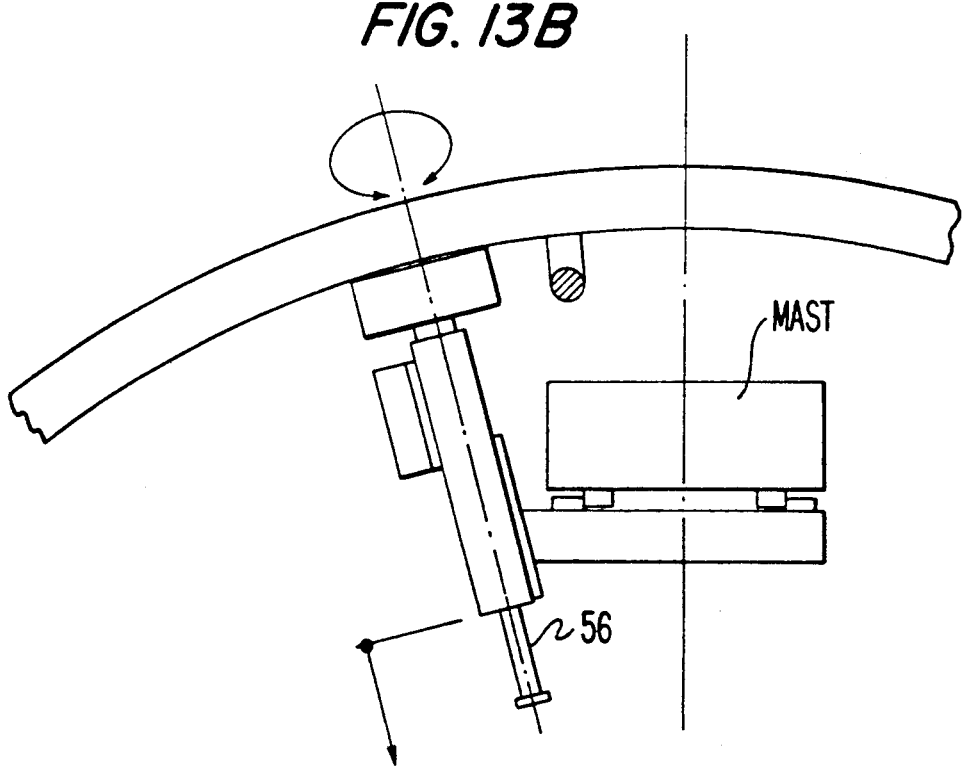

FIG. 1 also shows that at least one narrow side of mast 9 is provided with at least one second carrier 20 for receiving test instruments. Referring to FIGS. 2 and 13, this carrier can be displaced as desired relative to the longitudinal direction of the mast by a suitable drive mechanism 54 and in the direction toward the inner wall surface of pressure vessel 1, laterally to the longitudinal axis of the mast, by a suitable drive mechanism 56, and rotationally around the operating axis of the test instrument by a suitable drive mechanism 58. Second carrier 20, including its rotary drive, can be removed by means of a lance 21 (FIG. 3). FIG. 1 also shows that trailing cables 22 and 23 are provided with which the carrier and the test instruments disposed thereon are supplied with electric energy and through which the picked-up signals are carried away for evaluation.

FIGS. 2 and 3 show the arrangement once again in another way. The same components are given the same reference numerals. In order to give an impression of the size of the arrangement, an operator is drawn in at 24.

Figure 4:
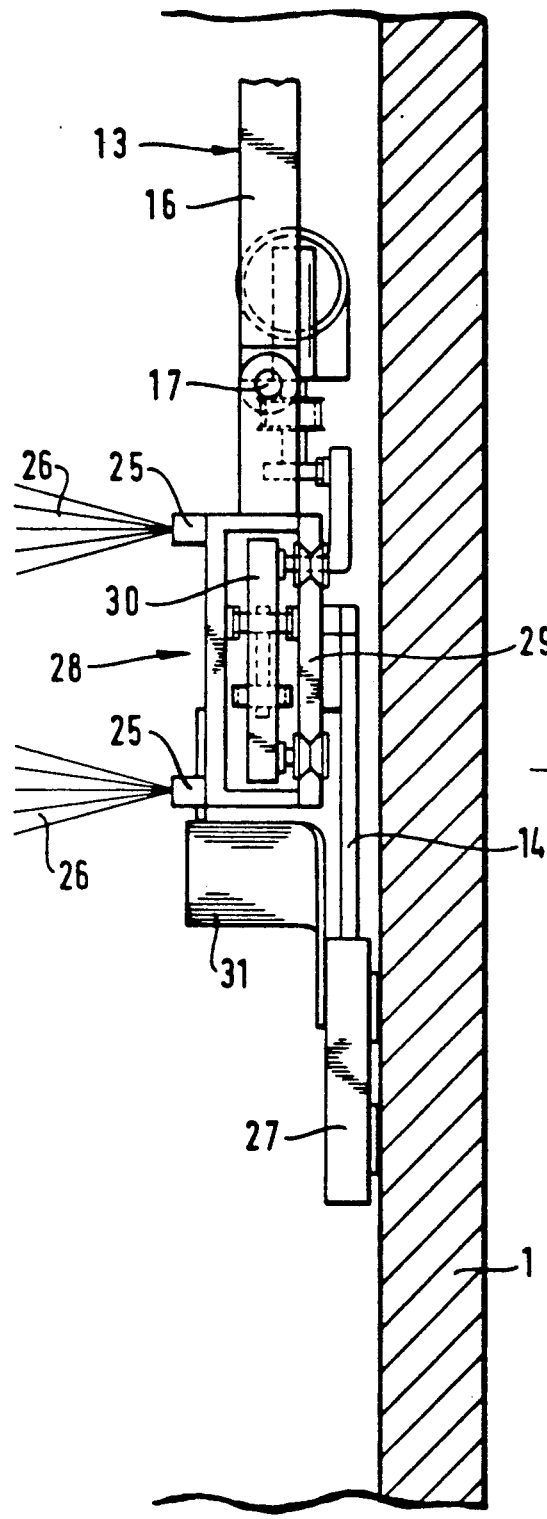
FIG. 4 is a schematic side view of the first carrier including a side view of reaction jets in the form of hydraulic water nozzles.

In order to accomplish that the first carrier together with the test instruments disposed thereon is pressed reliably against the interior of pressure vessel 1, carrier 14 is provided with hydraulic reaction jets 25, two of which are shown in FIG. 4. Once the carrier has been brought into the desired position, reaction jets 25 are turned on and shoot jets 26 of water out toward the rear. This causes test instruments 27 to be pressed against pressure vessel 1 in the desired manner.

Figure 5:
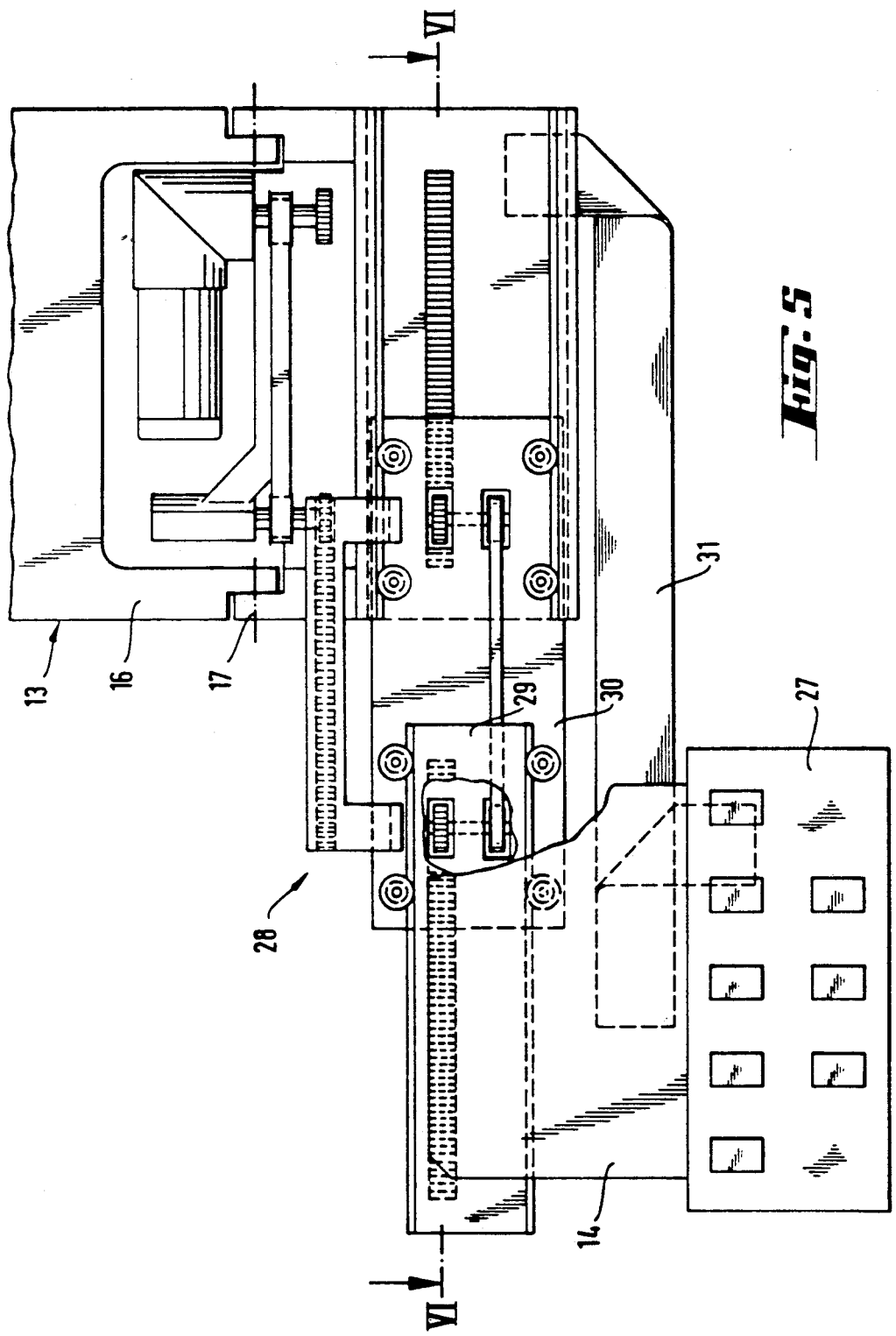
FIG. 5 is a simplified front view of the laterally displaceable first carrier and the double telescoping member.
Figure 6:
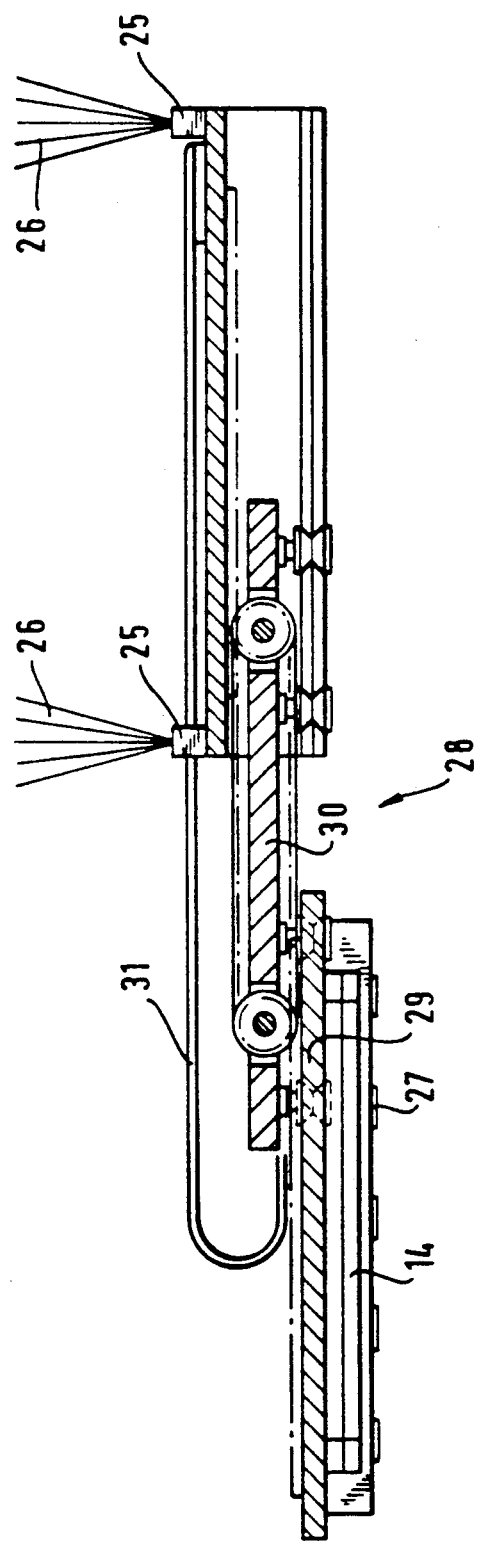
FIG. 6 is a cross-sectional view along line VI—VI of FIG. 5.

As already explained, carrier 14 can be moved out laterally which is preferably accomplished by way of a two-part telescoping member 28 whose tubes 29 and 30 are driven in a coordinated manner, with the telescoping member being connected with the end of deflectable belt 13. Carrier 14 is here again connected with the end of the belt by way of a broad trailing cable 31 through which the test instruments are supplied with energy and through which the picked-up signals are carried away. Preferably, flat cables composed of several juxtaposed stranded conductors as these are known from the computer art are employed as trailing cable 31. The arrangement is shown in a front view in FIG. 5 and in a cross-sectional view in FIG. 6.

Figures 7, 9:
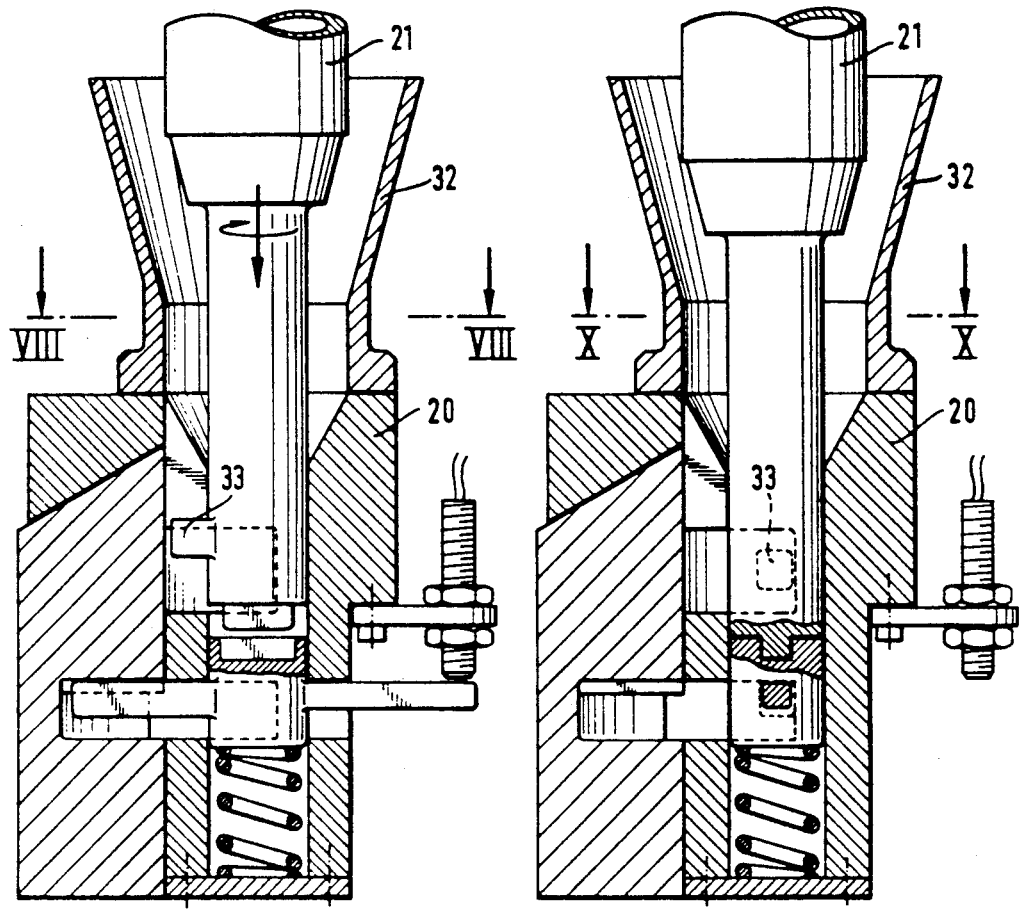
FIGS. 7, 8, 9 and 10 show basic views of the device for removing the second carrier with the aid of a lance.
Figures 8, 10:
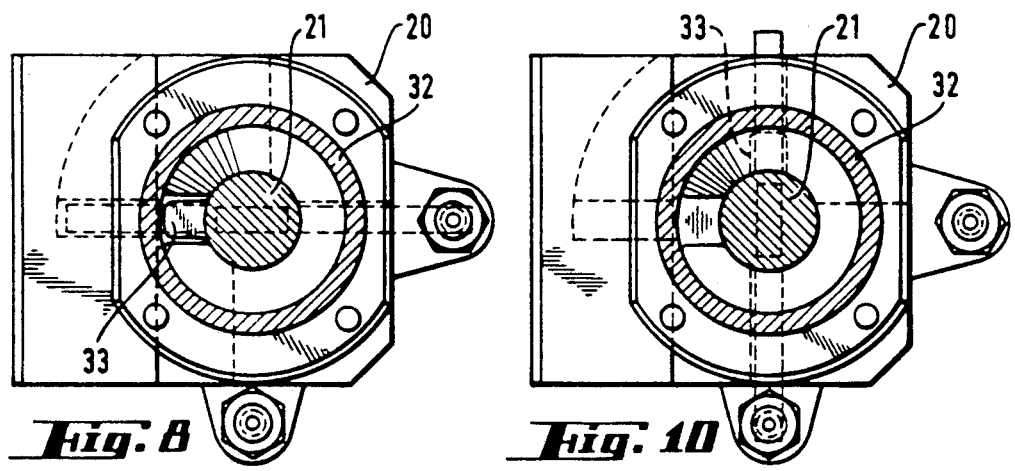

As already mentioned, at least one second carrier 20 is disposed on at least one narrow side of mast 9. Second carrier 20 also serves to accommodate test instruments and can be moved as desired in the direction of the longitudinal axis of the mast and of the interior surface of the pressure vessel, laterally to the longitudinal axis of the mast, and rotationally about the operating axis of the test instrument by way of a rotary drive mechanism. This second carrier, including its rotary drive, is preferably removable by means of a lance 21 (FIG. 3). Some details of it are shown in FIG. 7 to 10. To remove the second carrier, lance 21 is initially inserted into an opening provided for this purpose. To facilitate this, a guide funnel 32 is disposed on the top face of second carrier 20. At its lower end, lance 21 is provided with a switching nipple 33 which is introduced in the manner shown in FIGS. 7 and 8. Once the lance is introduced, the carrier continues to be firmly seated in its anchorage. Only after the lance has been turned by 90° about its vertical axis, is the carrier released from its previous fastening and a secure connection is established with the lance (FIGS. 9 and 10). Once this has been accomplished, the second carrier together with the instruments fastened thereon can be pulled upward by means of the lance.

Obviously, numerous and additional modifications and variations of the present invention are possible in light of the above teachings. It is therefore to be understood that within the scope of the appended claims, the invention may be practiced otherwise than as specifically claimed.

What is claimed is:

1. A manipulator device for use in non-destructive testing of an upright cylindrical nuclear reactor pressure vessel in which there is disposed a coaxially arranged likewise cylindrical nuclear fuel container, comprising:
   a first upper annular rail fastened to an upper edge of the pressure vessel;
   a second lower annular rail fastened to an upper edge of the nuclear fuel container;
   a bridge element displaceably mounted on said first annular rail;
   a vertical, hollow mast projecting into the pressure vessel and having an upper end mounted at said bridge and a lower end movably mounted to said second annular rail so as to be movable in a circumferential direction of the pressure vessel;
   a deflectable belt disposed for longitudinal displacement through said hollow mast, said belt exiting said hollow mast at a lower region of said mast and having an end extendable into an annular space between an inner wall surface of the pressure vessel and an outer wall surface of the nuclear fuel container; and
   a first test instrument carrier mounted at the end of said belt.

2. A device as defined in claim 1, wherein said belt is deflectable in a direction toward the inner wall surface of the pressure vessel.

3. A device as defined in claim 1, and further comprising drive motor means attached to said bridge and in operative connection with said first annular rail for moving said bridge along said first annular rail.

4. A device as defined in claim 3, and further comprising a drive mechanism attached to the lower end of said mast and in operative connection with said second annular rail; and coupling means coupling said drive motor means to said drive mechanism.

5. A device as defined in claim 4, wherein said first annular rail includes an annular gear and said drive motor means is in operative connection with said gear.

6. A device as defined in claim 1, wherein said belt comprises a link chain.

7. A device as defined in claim 1, wherein said first carrier includes a laterally displaceable portion which can be laterally moved out at the end of said belt.

8. A device as defined in claim 7, wherein said first carrier comprises a two-part telescoping member for effecting lateral displacement of said laterally displaceable portion.

9. A device as defined in claim 1, and further comprising hydraulic reaction jets attached to said first carrier for pressing said first carrier and a test instrument attached to said first carrier against the inner wall of the pressure vessel.

10. A device as defined in claim 1, wherein said mast includes a guide opening in a lower side region facing the inner wall of the pressure vessel and an adjustable swivel guide disposed in the vicinity of said guide opening for deflecting said belt in a direction toward the inner wall surface of the pressure vessel.

11. A device as defined in claim 1, wherein said mast has a narrow side, and said device further comprises a second test instrument carrier disposed at said narrow side, said second carrier being selectively movable in the longitudinal direction of said mast, in the direction toward the inner wall surface of the pressure vessel, and rotationally about an operating axis of a test instrument attached to said second carrier.

12. A device as defined in claim 11, wherein the second carrier includes a rotary drive for rotating a test instrument about the operating axis, and means for permitting removal of said second carrier, including its rotary drive, by way of a lance from said mast.

13. A device as defined in claim 1, wherein said upper and lower annular rings are removably mounted to the upper edges of the pressure vessel and the nuclear fuel container, respectively.

14. A device as defined in claim 1, wherein said bridge can be flanged to the mast at different levels. .

* * * * *

UNITED STATES PATENT AND TRADEMARK OFFICE
CERTIFICATE OF CORRECTION

PATENT NO. : 5,128,094
DATED : July 7th, 1992
INVENTOR(S) : Günter Müller et al.

It is certified that error appears in the above-identified patent and that said Letters Patent is hereby corrected as shown below:

On cover page at Item [30]: change "May 5, 1990" to --May 3, 1990--.

Signed and Sealed this

Seventh Day of September, 1993

Attest:

BRUCE LEHMAN

*Attesting Officer*      *Commissioner of Patents and Trademarks*